United States Patent [19]
Cumming et al.

[11] Patent Number: 6,153,220
[45] Date of Patent: Nov. 28, 2000

[54] TASTE-MASKED FORMULATIONS

[75] Inventors: Kenneth Iain Cumming; Elaine Harris, both of Dublin, Ireland

[73] Assignee: Elan Corporation, plc, Dublin, Ireland

[21] Appl. No.: 09/163,731

[22] Filed: Sep. 30, 1998

Related U.S. Application Data

[60] Provisional application No. 60/060,894, Oct. 3, 1997.

[51] Int. Cl.$^7$ .............................. A61K 9/14; A61K 9/20; A61K 9/22; A61K 9/46
[52] U.S. Cl. ..................... 424/464; 424/441; 424/465; 424/466; 424/468; 424/470; 424/489; 514/937; 514/974
[58] Field of Search ................................. 424/489, 464, 424/465, 441, 466, 468, 470

[56] References Cited

U.S. PATENT DOCUMENTS 4,708,867  11/1987  Hsiao ......................................... 424/80
4,760,093  7/1988  Blank et al. ............................. 514/629

*Primary Examiner*—James M. Spear
*Attorney, Agent, or Firm*—Kirsten A. Anderson

[57] ABSTRACT

A taste-masked micromatrix powder in which the ratio of a cationic copolymer synthesized form dimethylaminoethyl methacrylate and neutral methacrylic acid esters compared to a drug having poor organoleptic properties is greater than 2 to 1, preferably 4 to 1, most preferably 6 to 1 (wt/wt). Taste masked immediate release micromatrix powders can be formed by spray drying the drug and cationic copolymer whereas sustained release micromatrix powders can be formed by granulating controlled release powders, which can be made by spray drying the drug with a retarding polymer, with the cationic copolymer. The immediate release or sustained release taste-masked powders of this invention can be incorporated into conventional oral dosage forms such as sprinkles, suspension, fast melt tablets, chewable tablets or effervescent tablets.

18 Claims, No Drawings

TASTE-MASKED FORMULATIONS

This application claims the benefit of Provisional Application 60/060,894 filed Oct. 3, 1997.

FIELD OF THE INVENTION

The present invention relates to taste-masked pharmaceutical formulations. In particular, this invention relates to micromatrix powders containing a drug having poor organoleptic properties and a cationic copolymer synthesized from dimethylaminoethyl methacrylate and neutral methacrylic acid esters. These powders can be incorporated into several different final dosage forms such as sprinkles, suspensions and effervescent, fast melt or chewable tablets.

BACKGROUND OF THE INVENTION

The production of a palatable dosage form is very important for patient compliance. The masking of unpleasant tastes is therefore an important consideration in the formulation of many therapeutic agents and is achieved by minimizing direct contact between the active species and the taste receptors in the buccal cavity of the subject.

Cationic copolymers synthesized from dimethylaminoethyl methacrylate and neutral methacrylic acid esters such as Eudragit E 100 have been employed in various taste-masking formulations. For instance, U.S. Pat. No. 5,275,823 discloses a chewable tablet comprising a granulate of a histamine H2-receptor antagonist and optionally Eudragit E 100 and an admixture of a taste-masking extragranular water-insoluble hygroscopic excipient. While the purpose of the extragranular water-insoluble hygroscopic excipient is to reduce or eliminate the intensely bitter taste, Eudragit E 100 can be included in the granulate to provide extra taste-masking properties. Examples show a ratio of Eudragit E 100 to drug of 1 to 10.

U.S. Pat. No. 5,489,436 discloses a chewable medicament tablet comprising a medicament coated with a taste-masking amount of a polymer blend of dimethylaminoethyl methacrylate and neutral methacrylic acid esters and a polymer selected from cellulose acetate and cellulose triacetate. This coating blend is intended to achieve a balance between taste masking, dissolution and rate of bioavailability.

U.S. Pat. No. 4,708,867 discloses a mini pellet dosage form of prednisone comprising a nonpareil seed coated with a first layer of the drug and a second layer of a copolymer of dimethylaminoethyl methacrylate and methyl methacrylate.

U.S. Pat No. 5,013,557 discloses a spray-dried spheroidal microcapsule comprising 1–70 wt% sucralphate and 30–99 wt % of a polymer soluble in gastric fluids such as maltrin. The examples illustrate 1:1 sucralfate to maltrin microcapsules, which can be incorporated in chewable products.

U.S. Pat. No. 4,760,093 discloses a taste neutral powder form of spray-dried acetaminophen which consists essentially of about 60% to 74% by weight acetaminophen and about 26% to 40% by weight of a copolymer, cationic in character, based on dimethyaminoethyl methacrylate and neutral methacrylic acid esters.

SUMMARY OF THE INVENTION

However, none of the patents listed above teach the advantageous use of employing cationic copolymers synthesized from dimethylaminoethyl methacrylate and neutral methacrylic acid esters in amounts significantly greater than the amount of drug in need of taste masking to form with the drug a taste-masked micromatrix powder. These micromatrix powders can be used in oral dosage forms such as sprinkles, suspensions, chewable tablets, fast melt tablets and effervescent tablets without the unpleasant possibility of a taste-masking coating being breached by mastication or insufficient amounts of taste masker being present to provide adequate elimination of the unpleasant organoleptic properties of the drug.

Thus, the present invention provides a taste-masked micromatrix powder in which the ratio of the cationic copolymer synthesized from dimethylaminoethyl methacrylate and neutral methacrylic acid esters compared to a drug having poor organoleptic properties is greater than 2 to 1, preferably 4 to 1, most preferably 6 to 1 when compared weight to weight. The drug and the copolymer such as Eudragit E 100 comprise micromatrices having an average size from about 1 $\mu$m to 125 $\mu$m, preferably average particle sizes from about 5 $\mu$m to 30 $\mu$m. Preferably, the micromatrices are manufactured using a spray drying procedure. In this manner, the drug is completely taste masked, including those drugs having foul organoleptic properties, in particles sized to avoid exceeding the "mouth-feel" threshold.

Further, the taste-masked micromatrix powder of this invention is capable of not only masking drugs with undesirable taste characteristics but also controlling the rate at which the drug is delivered following oral administration to a subject such as a human. Drugs whose target dissolution profile calls for immediate release can be efficiently taste masked and delivered from micromatrix powders which contain primarily Eudragit E, which is soluble in gastric fluids, and the drug having poor organoleptic properties. Alternatively, drugs whose target dissolution profile requires controlled and/or sustained release over a period of time such as 30 minutes to 24 hours can be incorporated first into controlled release powders which comprise micromatrices of the drug and a retarding polymer such as by spraying drying the drug with the retarding polymer. Micromatrix taste-masked powders can then be made, for instance, by granulating the controlled release powders with the cationic copolymer synthesized from dimethylaminoethyl methacrylate and neutral methacrylic acid esters such that the amount of cationic copolymer is greater than twice the amount of drug based upon weight.

The drugs having poor organoleptic properties can be $H_2$ receptor antagonists, antibiotics, analgesics, cardiovascular agents, peptides or proteins, hormones, anti-migraine agents, anti-coagulant agents, anti-emetic agents, anti-hypertensive agents, narcotic antagonists, chelating agents, anti-anginal agents, chemotherapy agents, sedatives, anti-neoplastics, prostaglandins and antidiuretic agents, preferably nizatidine or roxatidine. The immediate release or sustained release taste-masked powders of this invention can be incorporated into conventional oral dosage forms such as sprinkles, suspension, chewable tablets, fast melt tablets or effervescent tablets.

DETAILED DESCRIPTION OF THE INVENTION

As used in this specification and appended claims, the singular forms "a", "an" and "the" include plural referents unless the content clearly dictates otherwise. Thus, for example, reference to a "a drug" includes reference to one or more drugs, and the like.

As used herein, the term "drug having poor organoleptic properties" refers to a drug or therapeutic agent possessing taste and/or odor characteristics which, when administered orally without any excipients, render the drug or therapeutic agent unpalatable to a subject. There is essentially no limitation on the type of drug having poor organoleptic properties which can be used in this invention other than to exclude those drugs which would be inappropriate to deliver to the subject orally. Representative drugs include, but are not limited to, $H_2$ receptor antagonists, antibiotics, analgesics, cardiovascular agents, peptides or proteins, hormones, anti-migraine agents, anti-coagulant agents, anti-emetic agents, anti-hypertensive agents, narcotic antagonists, chelating agents, anti-anginal agents, chemotherapy agents, sedatives, anti-neoplastics, prostaglandins, antidiuretic agents and the like. Typical drugs include but are not limited to nizatidine, cimetidine, ranitidine, famotidine, roxatidine, etinidine, lupitidine, nifentidine, niperitone, sulfotidine, tuvatidine, zaltidine, erythomycin, penicillin, ampicillin, roxithromycin, clarithromycin, psylium, ciprofloxacin, theophylline, nifedipine, prednisone, prednisolone, ketoprofen, acetaminophen, ibuprofen, dexibuprofen lysinate, flurbiprofen, naproxen, codeine, morphine, sodium diclofenac, acetylsalicylic acid, caffeine, pseudoephedrine, phenylpropanolamine, diphenhydramine, chlorpheniramine, dextromethorphan, berberine, loperamide, mefenamic acid, flufenamic acid, astemizole, terfenadine, certirizine, phenytoin, guiafenesin, N-acetylprocainamide HCl, pharmaceutically acceptable salts thereof and derivatives thereof.

Eudragit E 100, which is available from Rohm Pharma GmbH, Darmstadt, Germany, is a cationic polymer based on dimethylaminoethyl methacrylate and neutral methacrylates. It becomes water soluble via salt formation with acids, thus providing gastrosoluble film coatings. Eudragit E films swell and are permeable in water and buffer solutions above pH 5. It is soluble in gastric fluid below a pH of 5. The average molecular weight of Eudragit E is about 150,000 and it neither contains any plasticizers nor requires their addition for processing.

Spray dryers can be of the usual laboratory or commercial type. Suitable spray dryers are manufactured by Buchi Laboratoriums-Technik AG and by Niro Atomizer Inc. of Columbia, Md. A bench-scale Buchi spray dryer, Model B-191, was employed in the examples given herein.

The following examples illustrate the formation of the taste-masked pharmaceutical powders of this invention.

neutral methacrylic acid esters (e.g., Eudragit E 100), wherein the ratio (wt/wt) of copolymer to drug is greater than 2:1, and spray drying the solution/dispersion. For example, spray-dried Nizatidine powders are suitably prepared by dissolving 150 g of Eudragit E-100 in 800 ml acetone and then adding 200 ml distilled $H_2O$ and 25 g of Nizatidine, preferably NED free Nizatidine, to the solution (solvent system=acetone:$H_2O$ (80:20)). If desired, a flavorant or sweetener can be added to the solution such as 2.5 g aspartame or a sugar. Alternatively, the solvent system suitably can be ethanol:d$H_2O$ (80:20), 100% ethanol or 100% acetone and the like. The solution is spray dried such as using a Buchi B-191 spray dryer under the following initial conditions: Inlet temperature—85° C.; Outlet temperature—50° C.; Compresssed air—800 l/hr; Pump flow—75% and Aspirator—100%. Powders formed under these conditions are in the form of a micromatrix and typically are sized between 1 $\mu$m and 125 $\mu$m such as having average particle size of 5 to 30 $\mu$m (as measured by a Malvern Mastersizer MSS). If desired, the powders can be sieved. Characterization of these powders by scanning electron microsopy shows that they consist of discrete particles that are irregularly shaped. Typical recovery of product is 70–80% using this modest bench scale but can be greater at pilot and manufacturing scales.

Similarly, a taste-masked powder containing roxatidine in a micromatrix of Eudragit E can be prepared by dissolving Eudragit E in ethanol and adding roxatidine to this solution followed by spray drying. For instance, a suitably taste-masked powder was formed from Eudragit E/roxatidine in a 4:1 ratio (wt/wt). The theoretical loading for this batch was 20.0%; the actual loading was 19.95% and the size was D[v, 0.5] $\mu$m=31.77.

EXAMPLE 2

Optimization of drug:polymer ratio. Batches of spray-dried powders containing Nizatidine and Eudragit E 100 in varying ratios were prepared using the procedures of Example 1. The palatability of these powders were tested and the results are presented in Table 1

TABLE 1

| Batch | Formulation | | Solvent | Drug to Polymer ratio | Organoleptic Evaluation |
|---|---|---|---|---|---|
| A | Nizatidine | 7.5 g | Ethanol:$H_2O$ | 1:1 | very poor |
| | Eudragit E 100 | 7.5 g | (80:20) 250 ml | | |
| B | Nizatidine | 5 g | Ethanol:$H_2O$ | 1:2 | poor |
| | Eudragit E 100 | 10 g | 350 ml:5 ml | | |
| C | Nizatidine | 1.5 g | Ethanol:$H_2O$ | 1:4 | fair |
| | Eudragit E 100 | 6.0 g | (80:20) 100 ml | | |
| D | Nizatidine | 0.5 g | Ethanol:$H_2O$ | 1:6 | very good |
| | Eudragit E 100 | 3.0 g | (80:20) 100 ml | | |
| E | Nizatidine | 0.75 g | Ethanol:$H_2O$ | 1:8 | very good |
| | Eudragit E 100 | 6.0 g | (80:20) 100 ml | | |
| F | Nizatidine | 0.6 g | Ethanol:$H_2O$ | 1:10 | very good |
| | Eudragit E 100 | 6.0 g | (80:20) 100 mls | | |

EXAMPLE 1

Spray drying procedures. Spray-dried powders are formulated by preparing a solution or dispersion of a drug having poor organoleptic properties and a cationic copolymer synthesized from dimethylaminoethyl methacrylate and Organoleptic evaluation of these nizatidine powder batches indicated that an unacceptable level of bitterness was detected at a drug:polymer ratio of 1:2 but that powders containing greater amounts of the polymer were acceptable. Thus, taste-masked micromatrix powders can be formed by spray drying the drug with Eudragit E such that the amount of polymer present is at least twice the amount of drug present, more preferably at least 4 times the amount of drug present, most preferably at least 6 times the amount of drug present (wt/wt). Inclusion of a sweetener (aspartame) led to a 1:6:0.1 optimized ratio for drug:polymer:sweetener.

EXAMPLE 3

Tabletting of spray dried nizatidine powders. The taste-masked micromatrix powder can be combined with conventional pharmaceutical excipients to provide the final dosage form such as sprinkles, suspensions and effervescent, fast melt or chewable tablets. Examples of excipients include a sweetener, a diluent, a pH control agent, a flavor enhancer, a flavorant, a lubricant, a glident, a disintegrant or mixtures thereof.

Formulation of chewable tablets was carried out using the spray-dried Nizatidine:Eudragit-E-100:Aspartame powder. Several batches (summarised below) were prepared in which the major excipients were mannitol, xylitol, dextrose and aspartame; the flavors used were orange and raspberry. The tablets were compressed on a single station Fette, using 15 mm, round, concave punches.

TABLE 2

| Batch | G | H | I | J | K | L | M |
|---|---|---|---|---|---|---|---|
| Nizatidine Blend | 1666.0 | 1666.0 | — | — | — | — | — |
| Nizatidine Granulate | — | — | 559.9 | — | — | — | — |
| Nizatidine Powder | — | — | — | 262.5 | 262.5 | 262.5 | 262.5 |
| Nutraflow | 20.0 | 20.0 | 20.0 | 9.4 | 9.4 | 9.4 | 9.4 |
| Citric Acid | 68.0 | 55.0 | 55.0 | 13.0 | — | — | — |
| Sodium Bicarbonate | 55.0 | 55.0 | 55.0 | 13.0 | — | — | — |
| Dextrose | 154.0 | 154.0 | 631.3 | 90.3 | 245.7 | 116.3 | 116.3 |
| Mannitol | — | — | 631.3 | 262.5 | 131.2 | 262.5 | 262.5 |
| Xylitol | — | — | — | 262.5 | 262.5 | 262.5 | 262.5 |
| Aerosil 200 | 8.0 | 8.0 | — | 5.7 | 5.7 | 5.7 | 5.7 |
| Raspberry Flavor | — | 13.5 | — | — | — | — | 14.1 |
| Masking Agent | — | 13.5 | — | — | — | — | — |
| Orange Flavor | 20.0 | — | 30.0 | 14.1 | 14.1 | 14.1 | — |
| Aspartame | 3.0 | 5.0 | — | 4.7 | 4.7 | 4.7 | 4.7 |
| Mg. Stearate | 6.0 | 10.0 | 10.0 | 7.6 | 7.6 | 7.6 | 7.6 |

The nizatidine blend used in the batches G and H consisted of a 1:1:1 blend of (spray dried nizatidine:Eudragit E-100:aspartame in a ratio of 1:6:0.1) to mannitol to xylitol. This blend was combined with the remaining excipients and compressed into tablets. These formulations were acceptably taste masked.

The nizatidine granulate used in batch I is a spray granulate of spray-dried nizatidine powder (nizatidine: Eudragit E: aspartame in a ratio of 1:6:0.1) with aqueous PVP (K-25) 15.72 mg/tablet. The remaining excipients were combined with the granulate and compressed into tablets. The resulting tablet was not effectively taste masked. It was discovered that traditional wet granulation of the spray dried powders, such as with aqueous PVP, or granulation of the spray dried powders in a fluidized bed system lost most of the taste masking that was originally gained by spray drying the nizatidine with an amount of Eudragit E that was more than twice the amount of nizatidine present. One possible explanation is that water present in the granulating mixture causes a leeching of nizatidine from the micromatrix of the polymer/drug powder formed during spray drying.

The nizatidine powder used in batches J-M was spray dried nizatidine:Eudragit-E-100:aspartame in a ratio of 1:6:0.1. The powder was combined with the remaining excipients and compressed into tablets. These four batches were prepared after organoleptic evaluation indicated that the taste of the orange flavored tablets was improved if both the citric acid and the sodium bicarbonate were removed. All four of these chewable formulations were taste masked, especially, K, L and M.

Upon evaluation of the above tablets, the most pleasingly taste-masked formulations are orange flavored batches K and L, although some expressed a personal preference for the raspberry flavored tablets M. These preferred chewable tablets do not contain citric acid/sodium bicarbonate and contain a relatively large amount of dextrose.

Table 3 presents the potencies obtained for batches K and L as measured by HPLC using a Supelcosil LC-18-DB column, 15 cm×4.6 mm i.d.

TABLE 3

| Batch | mg/tab | % of Theoretical | % CV |
|---|---|---|---|
| K | 38.1 | 101.6 | 1.9 |
| L | 33.7 | 89.9 | 5 |

For nizatidine, a preferred dissolution profile in acidic media is release of greater than 75% of the dose in 30 min (essentially instant release). The in vitro dissolution for batches E and F were measured using USP II paddle method at 50 rpm, 37° C.±0.5° C. in 900 ml of pH 1.2 buffered medium (5 g NaCl plus 17.5 ml concentrated HCl per 2.5 L of deionized water). The resulting in vitro dissolution profiles as well as the profile for the reference product (AXID AR) are given in Table 4.

TABLE 4

| | % Released in Phosphate buffer pH1.2 | | |
|---|---|---|---|
| Time (min) Batch | AXID AR mean (N = 6) | K mean (N = 3) | L mean (N = 6) |
| 5 | 91.3 | 24.4 | 34.7 |
| 10 | 95.1 | 45.2 | 58.2 |
| 20 | 96.2 | 77.6 | 88.5 |
| 30 | 98.2 | 92.3 | 103.2 |
| 45 | 100.2 | 113.7 | 105.8 |
| 60 | 101.3 | 100.1 | 105.2 |

EXAMPLE 4

Controlled release taste-masked micromatrix powders. For some drugs, especially those whose target in vitro dissolution profile calls for controlled release over 30 min to 24 hours in addition to requiring taste-masking, an alternative method for making taste-masked micromatrix powders that includes the use of a retarding polymer can be used. For instance, a preferred target in vitro dissolution profile for roxatidine is release of from 25 to 45% of the therapeutic agent after one hour, release of from 45 to 65% after two hours and release of from about 55 to 75% after three hours.

Formulations having both excellent taste masking properties in addition to controlled release properties can be made by first spray drying the therapeutic agent with a polymer that is capable of retarding the release of the drug in acidic media to form a controlled release powder. Suitable retarding polymers include cellulose acetate phthalate (CAP), cellulose acetate butyrate (CAB) and ethylcellulose. The resulting controlled release powder is then granulated with an amount of Eudragit E that is at least twice the amount of the therapeutic agent (wt/wt) to form a granulate having a size less than about 125 μm. The resulting taste-masked micromatrix powder comprises controlled release therapeutic agent powder in a micromatrix of Eudragit E. The size of the controlled release powder is suitably controlled to be less than about 75 μm, preferably less than 50 μm so as to enable the size of the resulting micromatrix granulate (the taste-masked micromatrix powder) to be less than about 125 μm.

Alternatively, the controlled release powder can be formed according to the teaching of our U.S. Pat. No. 4,952,402, which reference is hereby incorporated by reference in its entirety. As above, the controlled release powder can be granulated with Eudragit E to form a micromatrix of Eudragit E and controlled release powder having a size less than about 125 μm.

Similar to the spray dried powders discussed above in Examples 1 and 2, the Eudragit E/controlled release powder micromatrices of this Example can be subsequently formulated into final dosage forms such as sprinkles, suspensions, and effervescent, fast melt or chewable tablets.

For instance, 15.6 g of ethylceilulose (7 cps) or 15.6 g of CAB (177-15S) can be dissolved in 2000 ml ethanol. 7.8 g of roxatidine can be added to the solution followed by spray drying to form the controlled release powder. Typical conditions for spray drying are: inlet temperature—85° C., outlet temperature—45–55° C., compressed air—750 l/hr, pump—75% and aspirator—100%. This controlled release powder can then be granulated using an ethanolic Eudragit E 100 solution (31.2 g Eudragit E) to form a taste-masked micromatrix powder.

Table 5 shows loading and size details for several batches of roxatidine controlled release powders formed by spray drying an ethanolic solution of roxatidine and the controlled release polymer.

TABLE 5

| Batch | Formulation | Theoretical loading (w/w %) | Actual loading (w/w %) | D [v, 0.5] μm |
|---|---|---|---|---|
| N | Ethylcellulose/Roxatidine (2:1) | 33.3 | 31.33 | 7.79 |
| O | Ethylcellulose:Roxatidine (4:1) | 20.0 | 21.47 | 6.36 |
| P | Ethylcellulose Roxatidine (3:1) | 25.0 | 23.61 | 10.21 |
| Q | CAB Roxatidine (4:1) | 20.0 | — | 91.07 |

EXAMPLE 5

Four 75 mg chewable Nizatidine tablet formulations comprising taste-masked micromatrix powder of Nizatidine manufactured according to this invention are shown in Table 6. All of these products demonstrated excellent taste-masking properties. Additionally, these products tasted pleasant, were easy to chew (having a smooth feel rather than chalky or gritty), and possessed a pleasant odor consistent with the flavor.

TABLE 6

| | R(a) | | S(b) | | T(c) | | V(d) | |
|---|---|---|---|---|---|---|---|---|
| Batch | Batch (g) | Tablet (g) | Batch (g) | Tablet (g) | Batch (g) | Tablet (g) | Batch (g) | Tablet (g) |
| *Nizatidine Powder | 100.003 | 0.536 | 100.010 | 0.536 | 72.501 | 0.535 | 100.027 | 0.535 |
| Xylisorb | 96.532 | 0.517 | 96.541 | 0.517 | 70.021 | 0.517 | 96.534 | 0.517 |
| Mannitol | 41.651 | 0.223 | 41.680 | 0.223 | 30.204 | 0.223 | 41.672 | 0.223 |
| Nutraflow | 3.364 | 0.018 | 3.402 | 0.018 | 2.452 | 0.018 | 3.371 | 0.018 |
| Dextrose | 82.355 | 0.441 | 82.416 | 0.441 | 59.713 | 0.441 | 82.394 | 0.441 |
| Mint Flavor | 5.102 | 0.027 | 5.081 | 0.027 | — | — | — | — |
| Orange Flavor | — | — | — | — | 3.661 | 0.027 | 5.075 | 0.027 |
| Aspartame | 1.703 | 0.009 | 1.703 | 0.009 | 1.238 | 0.009 | 1.706 | 0.009 |
| Aerosil 200 | 2.008 | 0.011 | 2.082 | 0.011 | 1.487 | 0.001 | 2.082 | 0.011 |
| Mg. Stearate | 3.407 | 0.018 | 3.381 | 0.018 | 2.452 | 0.018 | 3.413 | 0.018 |
| Actual Amt. Nizatidine (g) (mean) | 75.3% CV = 12.3 | | 82.3% CV = 7.3 | | 75.1% CV = 2.7 | | | |

| | Dissolution Profile | | | |
|---|---|---|---|---|
| Time | Mean (N = 6) | Mean (N = 6) | Mean (N = 6) | Mean (N = 6) |
| 5 min | 20.1 | 23 | 20.1 | |
| 10 min | 39.5 | 42.7 | 43 | |
| 20 min | 69.2 | 76.5 | 66.1 | |
| 30 min | 87.2 | 96 | 82.7 | |
| 45 min | 99.5 | 108.4 | 90.2 | |
| 60 min | 100.2 | 109.7 | 84.6 | |

*Nizatidine Spray Dried Micromatrix Powder containing Nizatidine and Eudragit E 100 in a 1:6 ratio (wt/wt)
(a) NED-containing; (b) NED free; (c) NED-containing; (d) NED free

What is claimed is:

1. A taste-masked pharmaceutical powder comprising micromatrices containing a drug having poor organoleptic properties and a cationic copolymer synthesized from dimethylaminoethyl methacrylate and neutral methacrylic acid esters, wherein the wt/wt ratio of the copolymer to the drug is greater than 2 to 1.

2. The taste-masked powder of claim 1, wherein the wt/wt ratio of the copolymer to the drug is greater than 4 to 1.

3. The taste-masked powder of claim 1, wherein the wt/wt ratio of the copolymer to the drug is greater than 6 to 1.

4. A taste-masked pharmaceutical dosage form comprising a therapeutically effective amount of the taste-masked powder of claim 1.

5. The taste-masked powder of claim 1, wherein the drug having poor organoleptic properties is selected from the group consisting of $H_2$ receptor antagonists, antibiotics, analgesics, cardiovascular agents, peptides or proteins, hormones, anti-migraine agents, anti-coagulant agents, anti-emetic agents, anti-hypertensive agents, narcotic antagonists, chelating agents, anti-anginal agents, chemotherapy agents, sedatives, anti-neoplastics, protaglandins and antidiuretic agents.

6. The taste-masked powder of claim 5, wherein the drug is nizatidine.

7. The taste-masked powder of claim 5, wherein the drug is roxatidine.

8. The taste-masked powder of claim 1, wherein the powder is formed by spray drying a solution or dispersion containing the drug having poor organoleptic properties and the copolymer.

9. The taste-masked powder of claim 1, wherein the micromatrices further comprise a retarding polymer.

10. The taste-masked powder of claim 9, wherein the retarding polymer and the drug having poor organoleptic properties comprise a controlled release powder.

11. The taste-masked powder of claim 10, wherein the taste-masked powder is formed by granulating the controlled release powder with the cationic copolymer synthesized from dimethylaminoethyl methacrylate and neutral methacrylic acid esters.

12. A taste-masked pharmaceutical powder comprising micromatrices containing a controlled release powder and a cationic copolymer synthesized from dimethylaminoethyl methacrylate and neutral methacrylic acid esters, wherein the controlled release powder comprises a drug having poor organoleptic properties and a retarding polymer and wherein the wt/wt ratio of the cationic copolymer to the drug is greater than 2 to 1.

13. The taste-masked powder of claim 12, wherein the wt/wt ratio of the copolymer to the drug is greater than 4 to 1.

14. The taste-masked powder of claim 12, wherein the wt/wt ratio of the a copolymer to the drug is greater than 6 to 1.

15. The taste-masked pharmaceutical dosage form of claim 4, wherein the dosage form is selected from the group consisting of sprinkles, suspensions, effervescent tablets, fast melt tablets and chewable tablets.

16. The taste-masked powder of claim 12, wherein the drug having poor organoleptic properties is selected from the group consisting of $H_2$ receptor antagonists, antibiotics, analgesics, cardiovascular agents, peptides or proteins, hormones, anti-migraine agents, anti-coagulant agents, anti-emetic agents, anti-hypertensive agents, narcotic antagonists, chelating agents, anti-anginal agents, chemotherapy agents, sedatives, anti-neoplastics, protaglandins and antidiuretic agents.

17. The taste-masked powder of claim 16, wherein the drug is nizatidine.

18. The taste-masked powder of claim 16, wherein the drug is roxatidine.

* * * * *